(12) United States Patent
Shultz et al.

(10) Patent No.: US 6,621,573 B2
(45) Date of Patent: Sep. 16, 2003

(54) GLASS CONTAINER INSPECTION MACHINE

(75) Inventors: Robert A. Shultz, Beaver Dam, NY (US); William J. Furnas, Elmira, NY (US)

(73) Assignee: Emhart Glass, S.A., Cham (CH)

( * ) Notice: Subject to any disclaimer, the term of this patent is extended or adjusted under 35 U.S.C. 154(b) by 210 days.

(21) Appl. No.: 09/794,868

(22) Filed: Feb. 27, 2001

(65) Prior Publication Data

US 2002/0118360 A1 Aug. 29, 2002

(51) Int. Cl.[7] ............................................. G01N 21/00
(52) U.S. Cl. ................................................... 356/239.4
(58) Field of Search ............................. 356/239.4, 394, 356/239.3, 237.5; 250/330, 342, 341, 358.1

(56) References Cited

U.S. PATENT DOCUMENTS

| | | | | |
|---|---|---|---|---|
| 4,820,932 A | * | 4/1989 | Miller | 250/559.06 |
| 5,250,809 A | * | 10/1993 | Nakata et al. | 250/330 |
| 5,995,219 A | * | 11/1999 | Tabata | 356/237.5 |

* cited by examiner

Primary Examiner—Tu T. Nguyen
(74) Attorney, Agent, or Firm—Spencer T. Smith

(57) ABSTRACT

A machine for inspecting the wall of a bottle having a surface decoration made up of lines. A two dimensional camera receives a transmitted image of the surface decoration and a computer scans the pixels to determine an area of selected pixels in which a selected pixel threshold is located. The aspect ratio of the area of selected pixels is determined and a bottle reject signal is issued in the event that the determined aspect ratio exceeds a predetermined value.

3 Claims, 3 Drawing Sheets

GLASS CONTAINER INSPECTION MACHINE

The present invention relates to container inspection machines.

BACKGROUND OF THE INVENTION

A formed bottle made in an I.S. (individual section) machine will be subject to any number of inspections to verify that the bottle is acceptable. In this inspection process the finish, shoulder, sidewall, and bottom of the bottle will be inspected to identify defects. When the wall (which herein includes the shoulder) is inspected, the defects encountered may be round or linear in appearance. Round defects include "seeds" which are very small bubbles in the glass, "blisters" which are large bubbles in the glass, "stones" which are small pieces of refractory or unmelted batch materials in the glass, and "dirt" which takes the form of carbon or other deposits.

When a decoration, made up of any number of lines, is defined on the bottle as it is formed, it conventionally is recognized as a defect by the inspection device.

OBJECT OF THE INVENTION

It is accordingly an object of the present invention to avoid the rejection of a bottle due to linear decorations on the shoulder of a bottle while rejecting the bottle when defects are present.

Other objects and advantages of the present invention will become apparent from the following portion of this specification and from the accompanying drawings, which illustrate in accordance with the mandate of the patent statutes a presently preferred embodiment incorporating the principles of the invention.

BRIEF DESCRIPTION OF THE PREFERRED EMBODIMENT

Figure 1:
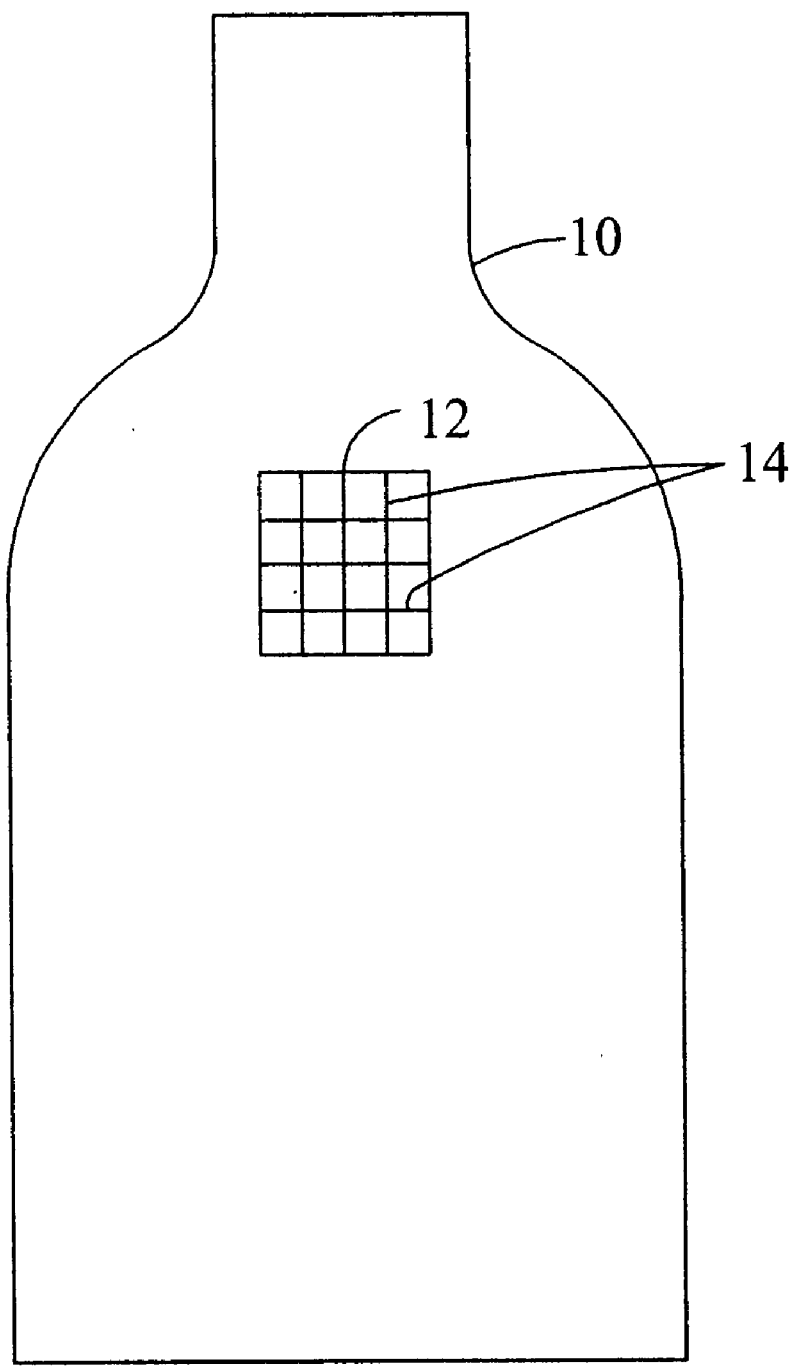
FIG. 1 is an elevational view of a bottle.
Figure 2:
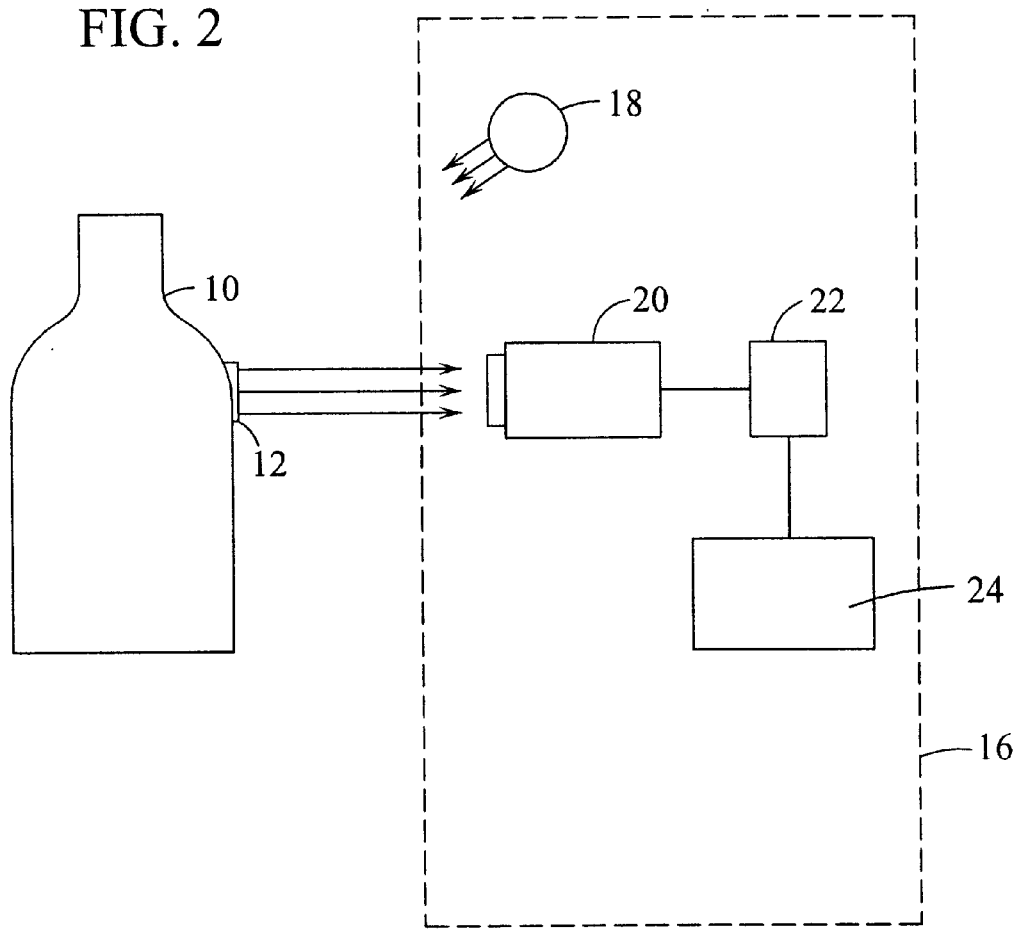
FIG. 2 is a schematic showing of in inspection machine inspecting the bottle shown in FIG. 1.

FIG. 1 illustrates a prior art formed glass container 10 which has a three dimensional decoration 12 on its surface. Such a decoration is formed by a corresponding three dimensional design on the surface of the blow mold which formed the bottle. As can be seen the decoration is made up of a number lines which are, in the simplest presentation, horizontal and vertical lines 14. In a conventional inspection machine 16 (FIG. 2), the wall of the bottle will be illuminated by a suitable light source 18 and the transmitted image of the wall will be received by a lens system 20 which presents the image on the imaging surface of a two dimensional CCD camera 22 which is evaluated by a computer 24.

Figure 3:
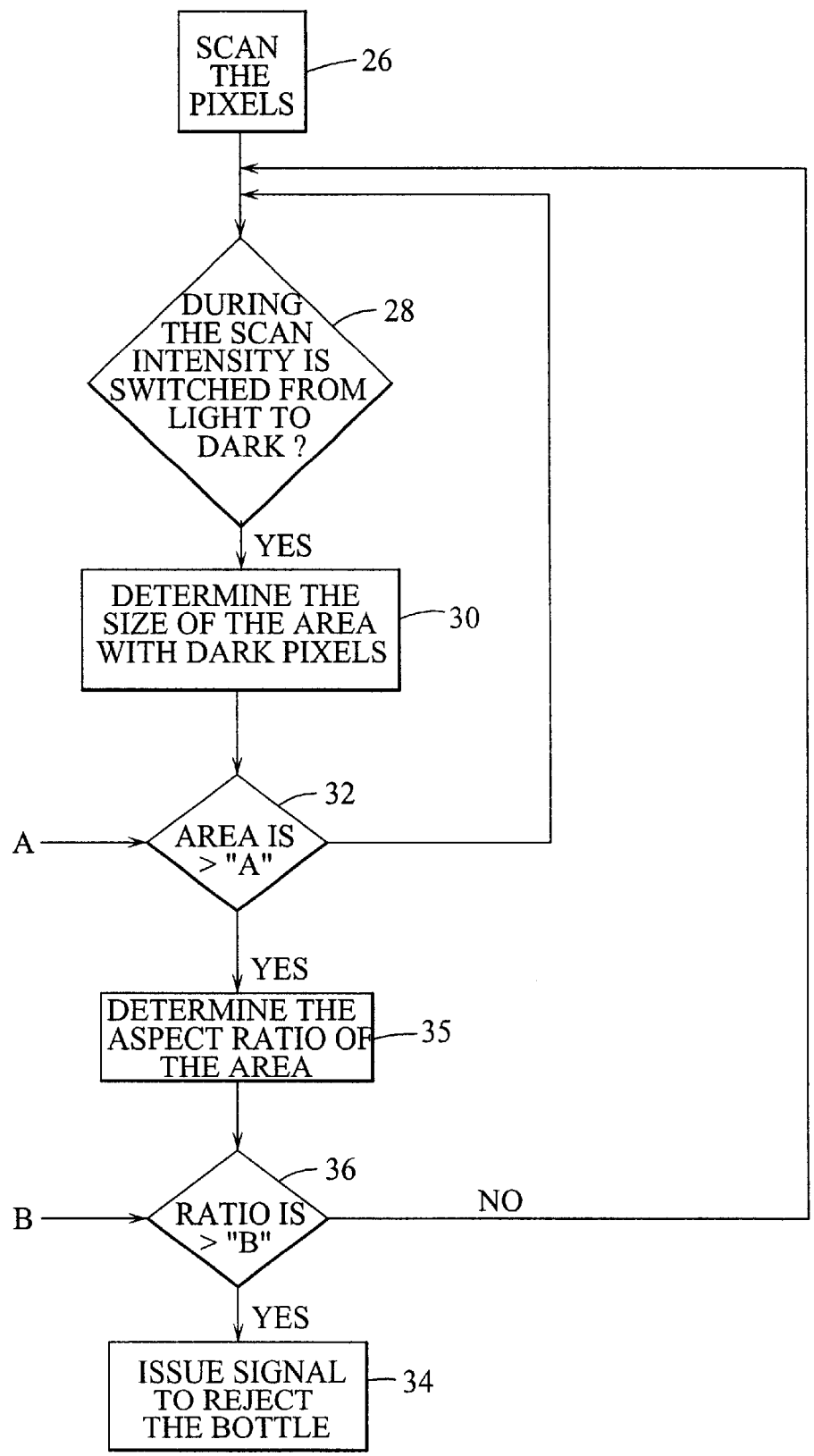
FIG. 3 is a logic diagram illustrating the operation of the computer which evaluates the image of the bottle.

The evaluation of the computer is shown in FIG. 3. The computer will Scan The Pixels 26 on the imaging surface of the camera and will determine whether During The Scan Intensity Has Switched From Light To Dark 28. If the answer is in the affirmative, the computer will Determine The Size Of The Area With Dark Pixels 30. In the event that the Area Is Greater Than "A" (the size threshold) 32, the computer will Determine The Aspect Ratio Of The Area 35 (the ratio of width to length or area to perimeter). In the event the Ratio is Greater Than B (the ratio threshold) 36, the computer will Issue Signal To Reject The Bottle 34. While the embodiment is illustrated with rejection occurring when the ratio is "Greater" than "B", this could also equate to "smaller" where the ratio was inverted, for example.

As shown, the operator can set "A" and "B" at values that will ignore the decoration. A stone, etc. will cause the bottle to be rejected if it will transmit a dark area greater than "A" having an aspect ratio greater than "B".

What is claimed is:

1. A machine for inspecting the wall of a bottle having a surface decoration made up of lines, comprising a two dimensional camera having an imaging surface which presents an image as an array of pixels, a lens system for receiving light transmitted from the surface decoration and directing the light to said imaging surface, a computer including
means for scanning the pixels,
means for determining an area "A" of pixels in which a selected pixel count is exceeded,
means for determining the aspect ratio "B" of area "A", and
means for issuing a bottle reject signal in the event that the determined aspect ratio exceeds a predetermined value.

2. A machine for inspecting the wall of a bottle having a surface decoration made up of lines according to claim 1, wherein "A" is settable.

3. A machine for inspecting the wall of a bottle having a surface decoration made up of lines according to claim 1, wherein "B" is settable.

* * * * *